(12) United States Patent
Yamashita et al.

(10) Patent No.: US 10,138,189 B2
(45) Date of Patent: Nov. 27, 2018

(54) METHODS FOR PRODUCING 2,6-DIMETHYL-1,5-HEPTADIEN-3-OL AND 2,6-DIMETHYL-1,5-HEPTADIEN-3-YL ACETATE

(71) Applicant: SHIN-ETSU CHEMICAL CO., LTD., Tokyo (JP)

(72) Inventors: Miyoshi Yamashita, Joetsu (JP); Takeshi Kinsho, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/653,393

(22) Filed: Jul. 18, 2017

(65) Prior Publication Data

US 2018/0029964 A1 Feb. 1, 2018

(30) Foreign Application Priority Data

Jul. 29, 2016 (JP) ................ 2016-149974

(51) Int. Cl.
*C07C 33/02* (2006.01)
*C07C 29/60* (2006.01)
*C07C 67/02* (2006.01)
*C07C 29/56* (2006.01)
*C07C 67/08* (2006.01)
*C07C 29/00* (2006.01)

(52) U.S. Cl.
CPC .............. *C07C 33/02* (2013.01); *C07C 29/00* (2013.01); *C07C 29/56* (2013.01); *C07C 29/60* (2013.01); *C07C 67/02* (2013.01); *C07C 67/08* (2013.01)

(58) Field of Classification Search
CPC ......... C07C 33/02; C07C 29/60; C07C 67/02; C07C 29/00; C07C 29/56; C07C 67/08
See application file for complete search history.

(56) References Cited

FOREIGN PATENT DOCUMENTS

JP S55-157526 A 12/1980
JP S57-163372 A 10/1982

OTHER PUBLICATIONS

Ghosh et al., "Copper(I) catalysis of olefin photoreactions. 15. Synthesis of cyclobutanated butyrolactones via copper(I)-catalyzed intermolecular photocycloadditions of homoallyl vinyl or diallyl ethers," J. Org. Chem., 1987, 52 (1), pp. 83-90.*
Itoh et al., "Systematic Synthesis of Multifluorinated α,α-Difluoro-γ-lactones through Intramolecular Radical Cyclization," J. Org. Chem., 1999, 64 (1), pp. 252-265.*
Nakai et al., "[2,3]-Wittig rearrangement of unsymmetrical bis-allylic ethers. Facile method for regio- and stereoselective synthesis of 1,5-dien-3-ols," J. Am. Chem. Soc., 1981, 103 (21), pp. 6492-6494.*
Bierl-Leonhardt et al., "Isolation, identification, synthesis, and bioassay of the pheromone of the comstock mealybug and some analogs," Journal of Chemical Ecology, 8(4) 1982, pp. 689-699.*
K. Mori et al., "Synthesis of the Optically Active Form of 2, 6-Dimethyl-1, 5-Heptadien-3-OL, Acetate, The Pheromone of the Comstock Mealybug", Tetrahedron, vol. 37, No. 15, pp. 2581-2583, (1981).
B. A. Bierl-Leonhardt et al., "Isolation, Identification, Synthesis, and Bioassay of the Pheromone of the Comstock Mealybug and Some Analogs", Journal of Chemical Ecology, vol. 8, No. 4, pp. 689-699, (1982).
R. I. Ishchenko et al., "Synthesis of the Racemic Sex Pheromone of Pseudococcus Comstocki", Chemical National Compound, vol. 25, No. 1, pp. 118-119, (1989).
P. Baeckstrom et al., "A One Pot Procedure for the Deoxygenation of the a,b-Unsaturated Ketones and a Synthesis of the Mealybug Pheromone", Synthetic Communications, vol. 20, No. 10, pp. 1481-1485, (1990).
D. W. McCullough et al., "Highly Efficient Terpenoid Pheromone Synthesis Via Regio- and Stereocontrolled Processing of Allyl-lithiums Generated by Reductive Lithiation of Allyl Phenyl Thioeth-ers", Tetrahedron, vol. 47, No. 47, pp. 9727-9736, (1991).

(Continued)

*Primary Examiner* — Pancham Bakshi
*Assistant Examiner* — Mark R Luderer
(74) *Attorney, Agent, or Firm* — Oliff PLC

(57) ABSTRACT

Provided are industrial and economical methods for producing 2,6-dimethyl-1,5-heptadien-3-yl acetate (3), which is, for example, a sex pheromone component of Comstock mealybug, and 2,6-dimethyl-1,5-heptadien-3-ol (2), which is an intermediate of the acetate (3). More specifically, provided are a method for producing 2,6-dimethyl-1,5-heptadien-3-ol comprising a step of subjecting 2-methyl-3-buten-2-yl 2-methyl-2-propenyl ether (1) to a rearrangement reaction in the presence of a base to obtain 2,6-dimethyl-1,5-heptadien-3-ol (2), and a method for producing 2,6-dimethyl-1,5-heptadien-3-yl acetate comprising a step of acetylating the produced 2,6-dimethyl-1,5-heptadien-3-ol (2) to obtain 2,6-dimethyl-1,5-heptadien-3-yl acetate (3).

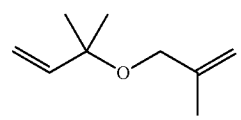

(1)

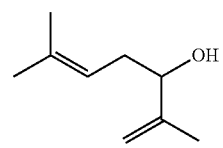

(2)

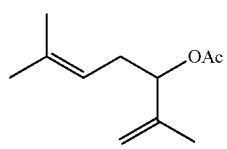

(3)

4 Claims, No Drawings

(56) References Cited

OTHER PUBLICATIONS

Nakai et al., "[2,3]-Wittig Rearrangement of Unsymmetrical Bis-Allylic Ethers. A Facile Method for Regio- and Stereoselective Synthesis of 1,5-Dien-3-ols," Communications to the Editor, Journal of the American Chemical Society, 1981, vol. 103, No. 21, pp. 6492-6494.

Itoh et al., "Systematic Synthesis of Multifluorinated alpha,alpha-Difluoro-gamma-lactones through Intramolecular Radical Cyclization," Journal of Organic Chemistry, 1999, vol. 64, No. 1, pp. 252-265.

Oct. 6, 2017 Extended Search Report issued in European Patent Application No. 17183435.1.

* cited by examiner

METHODS FOR PRODUCING 2,6-DIMETHYL-1,5-HEPTADIEN-3-OL AND 2,6-DIMETHYL-1,5-HEPTADIEN-3-YL ACETATE

BACKGROUND OF THE INVENTION

1. Field of the Invention

The invention relates to 2,6-dimethyl-1,5-heptadien-3-yl acetate, which is a sex pheromone component of Comstock mealybug (scientific name: *Pseudococcus comstocki*), and 2,6-dimethyl-1,5-heptadien-3-ol, which is an intermediate thereof.

2. Description of the Related Art

Since Comstock mealybug (scientific name: *Pseudococcus comstocki*) damages many fruit trees such as apples, pears, peaches and grapes and the excrement of this insect pest causes plant diseases, yield reduction and quality deterioration of these fruits have become a serious problem. At present, insecticides are used for the control of Comstock mealybug. However, they do not have a sufficient effect against the body of mealybugs covered with a waxy substance. Further, in order to prevent the insecticides from remaining on or in crops or prevent them from affecting the environment or health, there is a demand for the development of a new control technology such as mating disruption or mass trapping using the sex pheromone substance of the insect. Accordingly, an industrial and economical production method of the sex pheromone component is required to be established.

Mori et al. have reported that the sex pheromone component of Comstock mealybug is optically active (+)-2,6-dimethyl-1,5-heptadien-3-yl acetate (K. Mori et. al., Tetrahedron 37, 15, 2581(1981)). B. A. Bierl-Leonhardt et al. have reported that there is no difference in Comstock mealybug-attracting activity between optically active (+)-2,6-dimethyl-1,5-heptadien-3-yl acetate and a racemate (±)-2,6-dimethyl-1,5-heptadien-3-yl acetate which is a mixture of equal amounts of optical isomers (B. A. Bierl-Leonhardt et. al., J. Chem. Ecol. 8, 4, 689(1982)). Accordingly, to establish a control technology making use of the sex pheromone component, a method for producing the racemate (±)-2,6-dimethyl-1,5-heptadien-3-yl acetate is required to be established from the standpoint of economical control.

As a method for producing 2,6-dimethyl-1,5-heptadien-3-yl acetate of formula (3) below and a method for producing 2,6-dimethyl-1,5-heptadien-3-ol of formula (2) below, the following methods have been reported so far. They are a production method comprising a step of reacting isopentenyl bromide with methacrolein in the presence of a metal (JP 55-157526A), a production method comprising the steps of: converting 2,6-dimethyl-2,5-heptadiene to a mono-epoxy compound, and subjecting the mono-epoxy compound to rearrangement (B. A. Bierl-Leonhardt et. al., J. Chem. Ecol. 8, 4, 689(1982)), a production method comprising a step of reacting isobutenyl bromide with 3,4-epoxy-2-methylbutene in the presence of a metal lithium (R. I. Ishchenko et. al., Chem. Nat. Compd, 25, 1, 118 (1989)), a production method comprising a step of reducing a ketoalcohol by using p-toluenesulfonyl hydrazide and sodium cyanoborohydride wherein the ketoalcohol has been obtained from isopropyl methyl ketone and methacrolein (P. Baeckstrom et. al., Synth. Commun., 20, 10, 1481(1990)), and a production method comprising the steps of: reacting prenyl phenyl sulfide with lithium 1-(dimethylamino)naphthalenide, and then reacting the resulting reaction product with methacrolein in the presence of cerium chloride (D. W. McCullough et. al., Tetrahedron, 47, 47, 9727(1991)).

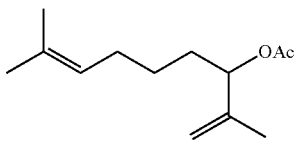

(3)

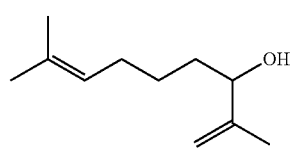

(2)

SUMMARY OF THE INVENTION

Regarding the method for producing 2,6-dimethyl-1,5-heptadien-3-yl acetate (3) and the method for producing 2,6-dimethyl-1,5-heptadien-3-ol (2) so far reported, the production method described in JP 55-157526A has such a problem that the yield of 2,6-dimethyl-1,5-heptadien-3-ol (2) is as extremely low as about 5%; the production method by B. A. Bierl-Leonhardt et. al. has such a problem that there is a great difficulty in synthesizing a large amount of the intended product because high-performance liquid chromatography is used for purifying an intermediate and 2,6-dimethyl-1,5-heptadien-3-yl acetate (3); and the production methods by R. I. Ishchenko et. al., by P. Baeckstrom et. al., and by D. W. McCullough et. al. have such a problem that starting materials or reagents are expensive and not easily obtained industrially in a large amount, wherein the starting materials or reagents include 4-epoxy-2-methylbutene in the method by R. I. Ishchenko et. al., p-toluenesulfonyl hydrazide and sodium cyanoborohydride in the method by P. Baeckstrom et. al., and lithium 1-(dimethylamino)naphthalenide and cerium chloride in the method by D. W. McCullough et. al. Thus, the conventional methods have various problems and are not suited for industrial and economical mass production.

With the forgoing in view, the invention has been made. An object of the invention is to overcome the problems of the conventional technologies and provide industrial and economical production methods for 2,6-dimethyl-1,5-heptadien-3-yl acetate (3), which is a sex pheromone component of Comstock mealybug, and 2,6-dimethyl-1,5-heptadien-3-ol (2) which is an intermediate thereof.

With a view to achieving the above-described object, the inventors have proceeded with investigation with sincerity. As a result, they have found that 2,6-dimethyl-1,5-heptadien-3-ol (2) can be produced in good yield. They have also found that 2,6-dimethyl-1,5-heptadien-3-yl acetate (3), which is a sex pheromone component of Comstock mealybug, can be produced industrially and economically in good yield through acetylation of the alcohol part of the resulting 2,6-dimethyl-1,5-heptadien-3-ol (2). Thus, they have completed the invention.

In one aspect of the invention, there is provided a method for producing 2,6-dimethyl-1,5-heptadien-3-ol comprising a step of subjecting 2-methyl-3-buten-2-yl2-methyl-2-propenyl ether of formula (1) below to a rearrangement reaction in the presence of a base to obtain 2,6-dimethyl-1,5-heptadien-3-ol (2).

In another aspect of the invention, there is provided a method for producing 2,6-dimethyl-1,5-heptadien-3-yl acetate comprising the steps of: subjecting 2-methyl-3-buten-2-yl 2-methyl-2-propenyl ether (1) to a rearrangement reaction in the presence of a base to obtain 2,6-dimethyl-1,5-heptadien-3-ol (2), and acetylating the 2,6-dimethyl-1,5-heptadien-3-ol (2) to obtain 2,6-dimethyl-1,5-heptadien-3-yl acetate (3).

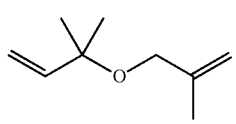

(1)

According to the invention, 2,6-dimethyl-1,5-heptadien-3-yl acetate (3), which is a sex pheromone component of Comstock mealybug, and 2,6-dimethyl-1,5-heptadien-3-ol (2), which is the intermediate thereof, can be produced efficiently and industrially at a low cost.

DETAILED DESCRIPTION OF THE PREFERRED EMBODIMENTS

First, starting material 2-methyl-3-buten-2-yl 2-methyl-2-propenyl ether (1) can be produced by a known method.

Examples of the method for producing the 2-methyl-3-buten-2-yl2-methyl-2-propenyl ether (1) include a production method comprising a step of reacting 2-methyl-3-buten-2-ol with 2-methyl-2-propen-1-yl halide in the presence of a base, a production method comprising a step of reacting 2-methyl-2-propen-1-ol with 2-methyl-3-buten-2-yl halide in the presence of a base, a production method comprising a step of reacting 2-methyl-3-buten-2-ol with a sulfonate ester such as 2-methyl-2-propen-1-yl methanesulfonate, 2-methyl-2-propen-1-yl benzenesulfonate or 2-methyl-2-propen-1-yl p-toluenesulfonate in the presence of a base, and a production method comprising a step of subjecting 2-methyl-3-buten-2-ol and 2-methyl-2-propen-1-ol to a dehydration reaction in the presence of an acid catalyst.

More specifically, for example, there is a production method comprising the steps of: reacting 2-methyl-3-buten-2-ol with sodium hydride to obtain a sodium alkoxide and then reacting the sodium alkoxide with 2-methyl-2-propen-1-yl halide (S. Ghosh et. al. 3. Org. Chem., 1987, 52, 83-90).

Next, the step of subjecting 2-methyl-3-buten-2-yl 2-methyl-2-propenyl ether (1) to a rearrangement reaction in the presence of a base to obtain 2,6-dimethyl-1,5-heptadien-3-ol (2) will be explained.

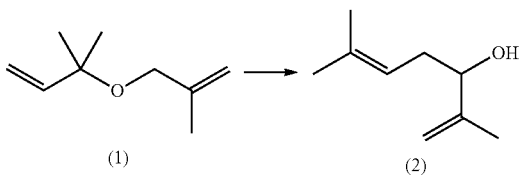

(1)              (2)

This rearrangement reaction generally proceeds in abstraction of an α-allyl proton or α'-allyl proton of diallyl ether by a base to form an anionic species, followed by a rearrangement reaction. There is a possibility of formation of a byproduct, depending on the abstraction position of these two allyl protons or rearrangement type.

According to the invention, the rearrangement is characterized in that 2,6-dimethyl-1,5-heptadien-3-ol (2) is produced from 2-methyl-3-buten-2-yl 2-methyl-2-propenyl ether (1) by one step and conveniently. Therefore, 2,6-dimethyl-1,5-heptadien-3-ol (2) can be produced with high selectivity and in high yield while reducing by-products formed by the difference in the abstraction position of allyl protons or rearrangement type.

This owes to the structural characteristics of 2-methyl-3-buten-2-yl 2-methyl-2-propenyl ether (1). More specifically, 2-methyl-3-buten-2-yl 2-methyl-2-propenyl ether (1) has two methyl groups at the allyl position on one side, so that abstraction of an allyl proton is limited to the allyl position on the other side. At the same time, the steric effect of the two methyl groups facilitates progress of the desired rearrangement type. The structural characteristics are considered to contribute to the progress of the rearrangement with high selectivity and in high yield.

According to the invention, the rearrangement proceeds by allowing a base to act on the diallyl ether with optional cooling or heating.

Examples of the base to be used in the rearrangement include metal alkoxides such as sodium methoxide, sodium ethoxide, sodium t-butoxide, lithium methoxide, lithium ethoxide, lithium t-butoxide, potassium methoxide, potassium ethoxide and potassium t-butoxide; organometallic compounds including organolithium reagents such as methyllithium, ethyllithium, n-butyllithium, t-butyllithium and phenyllithium, and Grignard reagents such as methyl magnesium chloride; and metal amides including lithium amides such as lithium amide, lithium diisopropyl amide and lithium hexamethyldisilazide, and sodium amides such as sodium amide, sodium diisopropylamide and sodium hexamethyldisilazide. The base may be used singly or in combination of two or more. Of these examples of the base, lithium t-butoxide, n-butyllithium, phenyllithium, sodium amide, lithium diisopropylamide and lithium hexamethyldisilazide are preferable from the standpoint of reactivity and selectivity of the rearrangement reaction.

The amount of the base to be used in the rearrangement reaction is preferably from 1.0 mol to 2.0 mol per mol of 2-methyl-3-buten-2-yl2-methyl-2-propenyl ether (1). It is more preferably from 1.1 mol to 1.4 mol per mol of 2-methyl-3-buten-2-yl 2-methyl-2-propenyl ether (1) from the standpoint of reactivity and yield.

The solvent to be used in the rearrangement reaction is not particularly limited insofar as it does not adversely affect the base. Examples of the solvent include ethers such as diethyl ether, tetrahydrofuran, cyclopentyl methyl ether, methyl t-butyl ether and 1,4-dioxane. The solvent may be used singly or in combination of two or more. Of these examples of the solvent, tetrahydrofuran, 1,4-dioxane and diethyl ether are preferable from the standpoint of reactivity and yield. A solvent selected from hydrocarbons inert to the reaction such as pentane, hexane, heptane, cyclohexane, ethylcyclohexane, benzene, toluene and xylene may be added further.

The amount of the solvent to be used in the rearrangement reaction is preferably from 100 g to 3000 g per mol of 2-methyl-3-buten-2-yl 2-methyl-2-propenyl ether (1). It is more preferably from 400 g to 1500 g per mol of 2-methyl-3-buten-2-yl 2-methyl-2-propenyl ether (1) from the standpoint of economy and reactivity.

The temperature of the reaction mixture at which the base is added dropwise to 2-methyl-3-buten-2-yl 2-methyl-2-propenyl ether (1), or at which 2-methyl-3-buten-2-yl 2-methyl-2-propenyl ether (1) is added dropwise to the base in the rearrangement reaction, is preferably from −78° C. to 80° C. It is more preferably from −40° C. to 30° C., still more preferably from −10° C. to 25° C., particularly preferably from −10° C. to 5° C., from the standpoint of selectivity and yield.

The reaction temperature for the rearrangement reaction after the dropwise addition of the base to 2-methyl-3-buten-2-yl 2-methyl-2-propenyl ether (1) or after the dropwise addition of 2-methyl-3-buten-2-yl 2-methyl-2-propenyl ether (1) to the base is preferably from −78° C. to 80° C. It is more preferably from −40° C. to 30° C., still more preferably from −10° C. to 25° C. from the standpoint of selectivity and yield.

Next, the step of acetylating 2,6-dimethyl-1,5-heptadien-3-ol of formula (2) below to obtain 2,6-dimethyl-1,5-heptadien-3-yl acetate of formula (3) below will be explained.

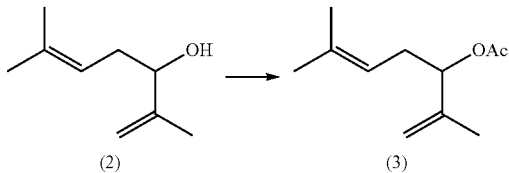

(2)                    (3)

The step for acetylating 2,6-dimethyl-1,5-heptadien-3-ol (2), which is an alcohol compound, to obtain 2,6-dimethyl-1,5-heptadien-3-yl acetate (3), is not particularly limited and a known acetylation method can be applied to the step.

Examples of the acetylation reaction include a reaction between the alcohol compound and an acetylating agent, a dehydration reaction between the alcohol compound and acetic acid, an ester exchange reaction between the alcohol compound and an acetate ester, and an acetoxylation reaction of acetic acid or the like and an alkylating agent obtained by conversion of the alcohol compound.

Examples of the acetylating agent to be used in the acetylation reaction include acetyl chloride, acetyl bromide and acetic anhydride.

The amount of the acetylating agent to be used is preferably from 1.0 mol to 30.0 mol per mol of the alcohol compound. It is more preferably from 1.0 mol to 5.0 mol per mol of the alcohol compound from the standpoint of economy.

The reaction between the alcohol compound and the acetylating agent can be usually carried out in the presence of a base or a catalyst.

Examples of the base to be used in the acetylation reaction with the acetylating agent include amines such as triethylamine, pyridine, N,N-dimethylaminopyridine and N,N-dimethylaniline; organolithium compounds such as n-butyllithium, methyllithium and phenyllithium; metal hydroxides such as sodium hydroxide and potassium hydroxide; and metal carbonates such as potassium carbonate, sodium carbonate and sodium hydrogen carbonate.

The amount of the base to be used in the acetylation reaction is preferably from 1.0 mol to 50.0 mol per mol of the alcohol compound. It is more preferably from 1.0 mol to 10.0 mol per mol of the alcohol compound from the standpoint of economy.

Examples of the catalyst to be used in the acetylation reaction in which acetic anhydride is used as the acetylating agent include inorganic acids such as hydrochloric acid, hydrobromic acid, nitric acid and sulfuric acid; sulfonic acids such as methanesulfonic acid, benzenesulfonic acid and p-toluenesulfonic acid; Lewis acids such as aluminum trichloride, aluminum isopropoxide, zinc chloride, boron trifluoride, boron trichloride, tin tetrachloride, dibutyltin dichloride, titanium tetrachloride and titanium(IV) isopropoxide; and metal acetates such as sodium acetate and potassium acetate.

The amount of the catalyst to be used in the acetylation reaction with the acetylating agent is preferably from 0.001 mol to 1.0 mol per mol of the alcohol compound. It is more preferably from 0.005 mol to 0.2 mol per mol of the alcohol compound from the standpoint of economy.

A solvent to be used in the acetylation reaction with the acetylating agent may be selected from solvents not adversely affecting the alcohol compound, the acetylating agent, the base or the catalyst. Examples of the solvent include halogen-based solvents such as methylene chloride and chloroform; hydrocarbons such as hexane, heptane, benzene and toluene; ethers such as diethyl ether, tetrahydrofuran, 1,4-dioxane and ethylene glycol dimethyl ether; nitrile-based solvents such as acetonitrile; ketones such as acetone, methyl ethyl ketone and diisobutyl ketone; esters such as ethyl acetate and butyl acetate; and aprotic polar solvents such as N,N-dimethylformamide, N,N-dimethylacetamide, dimethylsulfoxide and hexamethylphosphoric triamide. The solvent may be used singly or in combination of two or more. Although depending on a type of acetylating agent, the acetylation reaction may be carried out without a solvent.

The amount of the solvent to be used in the acetylation reaction with the acetylating agent is preferably from 0.0 g to 2000.0 g per mol of the alcohol compound. It is more preferably from 0.0 g to 500.0 g per mol of the alcohol compound from the standpoint of economy.

The reaction temperature for the acetylation reaction with the acetylating agent is preferably from −78° C. to 120° C., more preferably from −30° C. to 80° C., from the standpoint of reactivity.

The dehydration reaction between the alcohol compound and acetic acid can be usually carried out in the presence of an acid or Lewis acid catalyst.

Examples of the catalyst to be used in the dehydration reaction include inorganic acids such as hydrochloric acid, hydrobromic acid, nitric acid and sulfuric acid; organic acids such as trichloroacetic acid, trifluoroacetic acid, methanesulfonic acid, benzenesulfonic acid and p-toluenesulfonic acid; and Lewis acids such as aluminum trichloride, dichloroaluminum ethoxide, aluminum ethoxide, aluminum isopropoxide, zinc diisopropoxide, zinc diethoxide, zinc dimethoxide, zinc chloride, boron trifluoride, boron trichloride, tin tetrachloride, dibutyltin dichloride, dibutyltin dimethoxide, dibutyltin oxide, titanium tetrachloride, titanium tetrabromide, titanium(IV) methoxide, titanium(IV) ethoxide and titanium(IV) isopropoxide. The catalyst may be used singly or in combination of two or more.

The amount of the catalyst to be used in the dehydration reaction is preferably from 0.001 mol to 1.0 mol per mol of the alcohol compound. It is more preferably from 0.05 mol to 0.1 mol per mol of the alcohol compound from the standpoint of economy and reactivity.

The dehydration reaction between the alcohol compound and acetic acid can be carried out while removing water as a byproduct generated in the reaction. Examples of water-removal include distillation off of water by azeotropic distillation with the reaction solvent under normal pressure or reduced pressure, and addition of a dehydrating agent such as anhydrous magnesium sulfate, a molecular sieve or dicyclohexylcarbodiimide to the reaction system.

A solvent to be used in the dehydration reaction is selected from solvents not adversely affecting the catalyst. Examples of the solvent include halogen-based solvents such as methylene chloride and chloroform; hydrocarbons such as hexane, heptane, benzene and toluene; ethers such as diethyl ether, tetrahydrofuran, 1,4-dioxane and ethylene glycol dimethyl ether; nitrile-based solvents such as acetonitrile; ketones such as acetone, methyl ethyl ketone and diisobutyl ketone; and esters such as ethyl acetate and butyl acetate. The solvent may be used singly or in combination of two or more.

The amount of the solvent to be used in the dehydration reaction is preferably from 0.0 g to 2000.0 g per mol of the alcohol compound. It is more preferably from 0.0 g to 500.0 g per mol of the alcohol compound from the standpoint of economy.

The reaction temperature for the dehydration reaction between the alcohol compound and acetic acid can be appropriately selected depending on the kind of the catalyst. In general, it is preferably from −30° C. to 200° C. It is more preferably from 25° C. to 100° C. from the standpoint of reactivity and yield. When water generated as a byproduct is removed by azeotropic distillation with the solvent, the reaction temperature is preferably not less than the azeotropic point of the solvent and the water under normal pressure or reduced pressure.

The ester exchange reaction between the alcohol compound and an acetate ester is usually carried out in the presence of a catalyst. The reaction can be accelerated by removing, under normal pressure or reduced pressure, an alcohol as a byproduct generated from the acetate ester during the reaction.

Examples of the acetate ester to be used in the ester exchange reaction may include an acetate ester such as methyl acetate, ethyl acetate, propyl acetate, butyl acetate and phenyl acetate. Of these examples of the acetate ester, methyl acetate and ethyl acetate are preferable from the standpoint of economy, reactivity, and easy removal of an alcohol as a byproduct generated from the acetate ester.

The amount of the acetate ester to be used in the ester exchange reaction is preferably from 1.0 mol to 30.0 mol, more preferably from 1.0 mol to 5.0 mol per mol of the alcohol compound.

Examples of the catalyst to be used in the ester exchange reaction include acids such as hydrochloric acid, sulfuric acid, trifluoroacetic acid, methanesulfonic acid, benzenesulfonic acid, p-toluenesulfonic acid and Amberlyst® 15; alkali metal salts of an alcohol such as sodium methoxide, sodium ethoxide and potassium t-butoxide; metal carboxylates such as sodium acetate, potassium acetate, calcium acetate, tin acetate, zinc acetate and aluminum acetate; and Lewis acids such as aluminum trichloride, aluminum ethoxide, aluminum isopropoxide, zinc diisopropoxide, zinc diethoxide, zinc dimethoxide, zinc chloride, boron trifluoride, boron trichloride, tin tetrachloride, dibutyltin dichloride, dibutyltin dimethoxide, dibutyltin oxide, titanium tetrachloride, titanium tetrabromide, titanium(IV) methoxide, titanium(IV) ethoxide and titanium(IV) isopropoxide.

The amount of the catalyst to be used in the ester exchange reaction is preferably from 0.001 mol to 1.0 mol, more preferably from 0.005 mol to 0.05 mol per mol of the alcohol compound.

A solvent to be used in the ester exchange reaction may be selected from solvents not adversely affecting the catalyst. Examples of the solvent include halogen-based solvents such as methylene chloride and chloroform; hydrocarbons such as hexane, heptane, benzene and toluene; ethers such as diethyl ether, tetrahydrofuran, 1,4-dioxane and ethylene glycol dimethyl ether; nitrile-based solvents such as acetonitrile; ketones such as acetone, methyl ethyl ketone and diisobutyl ketone; and esters such as ethyl acetate and butyl acetate. The solvent may be used singly or in combination of two or more. The reaction may also be carried out without a solvent by using only the alcohol compound, the acetate ester and the catalyst.

The amount of the solvent to be used in the ester exchange reaction is preferably from 0.0 g to 2000.0 g per mol of the alcohol compound. It is more preferably from 0.0 g to 500.0 g per mol of the alcohol compound from the standpoint of economy.

The reaction temperature for the ester exchange reaction can be appropriately selected depending on the kinds of the acetate ester and catalyst. In general, the reaction temperature is preferably from 0° C. to 200° C., more preferably from 50° C. to 160° C. When an alcohol as a byproduct generated from the acetate ester during the reaction is removed to accelerate the reaction, the reaction temperature is preferably not less than the boiling point of the alcohol to be removed under normal pressure or reduced pressure.

The acetoxylation reaction of acetic acid or the like and an alkylating agent converted from the alcohol compound is usually carried out by converting the alcohol compound into an alkylating agent corresponding thereto, and then reacting the alkylating agent with acetic acid in the presence of a base, wherein examples of the alkylating agent include a halide such as chloride, bromide and iodide, and a sulfonate ester such as methanesulfonate ester, benzenesulfonate ester and p-toluenesulfonate ester. Alternatively, a metal acetate such as sodium acetate or potassium acetate available instead of acetic acid may be used in the absence of a base.

The conversion of the alcohol compound into a corresponding alkylating agent and the acetoxylation of the alkylating agent and acetic acid or the like may include an embodiment in which the alcohol compound is converted into a corresponding alkylating agent and then acetoxylated in situ. They may include another embodiment in which the reaction for the conversion of the alcohol compound into a corresponding alkylating agent is terminated, the organic layer is washed and subjected to removal of the solvent and then optional purification to obtain the alkylating agent, and the alkylating agent is acetoxylated with acetic acid or the like.

Examples of the reaction of converting the alcohol compound into a corresponding alkylating agent include a reaction of converting an alcohol compound into a corresponding chloride, bromide or iodide by a halogenating agent and a reaction of converting the alcohol compound into a corresponding sulfonate ester by a sulfonylating agent.

Examples of the halogenating agent include a chlorinating agent such as hydrochloric acid, phosphorus trichloride, thionyl chloride, carbon tetrachloride, methanesulfonyl chloride and p-toluenesulfonyl chloride; a brominating agent such as hydrobromic acid, phosphorus tribromide, thionyl bromide and carbon tetrabromide; and an iodizing agent such as hydroiodic acid, potassium iodide and phosphorus triiodide.

Examples of the sulfonylating agent include methanesulfonyl chloride, benzenesulfonyl chloride and p-toluenesulfonyl chloride.

The amount of the halogenating agent or sulfonylating agent to be used in the reaction of converting the alcohol compound into a corresponding alkylating agent is preferably from 1.0 mol to 50.0 mol per mol of the alcohol compound. It is more preferably from 1.0 mol to 10.0 mol per mol of the alcohol compound from the standpoint of economy.

A solvent to be used in the reaction of converting the alcohol compound into a corresponding alkylating agent may be selected from solvents not adversely affecting reactive species. Examples of the solvent include halogen-based solvents such as methylene chloride and chloroform; hydrocarbons such as hexane, heptane, benzene and toluene; ethers such as diethyl ether, tetrahydrofuran, 1,4-dioxane and ethylene glycol dimethyl ether; nitrile-based solvents such as acetonitrile; ketones such as acetone, methyl ethyl ketone and diisobutyl ketone; esters such as ethyl acetate and butyl acetate; and aprotic polar solvents such as N,N-dimethylformamide, N,N-dimethylacetamide, dimethylsulfoxide and hexamethylphosphoric triamide. The solvent may be used singly or in combination of two or more.

The amount of the solvent to be used in the reaction of converting the alcohol compound into a corresponding alkylating agent is preferably from 0.0 g to 2000.0 g per mol of the alcohol compound. It is more preferably from 0.0 g to 500.0 g per mol of the alcohol compound from the standpoint of economy.

The reaction temperature for the reaction of converting the alcohol compound into a corresponding alkylating agent is preferably from −30° C. to 250° C. from the standpoint of reactivity and yield. It is more preferably from 0° C. to 180° C. from the standpoint of reactivity and yield.

The amount of acetic acid or metal acetate to be used in the acetoxylation reaction of the alkylating agent thus obtained is preferably from 1.0 mol to 50.0 mol per mol of the alkylating agent. It is more preferably from 1.0 mol to 10.0 mol per mol of the alkylating agent from the standpoint of economy.

Examples of the base to be used in the acetoxylation reaction of the alkylating agent include amines such as triethylamine, pyridine, N,N-dimethylaminopyridine and dimethylaniline; organolithium compounds such as n-butyllithium, methyllithium and phenyllithium; metal hydroxides such as sodium hydroxide and potassium hydroxide; metal carbonates such as potassium carbonate, sodium carbonate and sodium hydrogen carbonate; and metal hydrides such as sodium hydride and potassium hydride.

The amount of the base to be used in the acetoxylation reaction of the alkylating agent is preferably from 1.0 mol to 50.0 mol per mol of the alkylating agent. It is more preferably from 1.0 mol to 10.0 mol per mol of the alkylating agent from the standpoint of economy.

A solvent to be used in the acetoxylation reaction of the alkylating agent may be selected from solvents not adversely affecting reactive species. Examples of the solvent include halogen-based solvents such as methylene chloride and chloroform; hydrocarbons such as hexane, heptane, benzene and toluene; ethers such as diethyl ether, tetrahydrofuran, 1,4-dioxane and ethylene glycol dimethyl ether; nitrile-based solvents such as acetonitrile; ketones such as acetone, methyl ethyl ketone and diisobutyl ketone; esters such as ethyl acetate and butyl acetate; and aprotic polar solvents such as N,N-dimethylformamide, N,N-dimethylacetamide, dimethylsulfoxide and hexamethylphosphoric triamide. The solvent may be used singly or in combination of two or more.

The amount of the solvent to be used in the acetoxylation reaction of the alkylating agent is preferably from 0.0 g to 2000.0 g per mol of the alkylating agent. It is more preferably from 0.0 g to 500.0 g per mol of the alkylating agent from the standpoint of economy.

The reaction temperature for the acetoxylation reaction of the alkylating agent is preferably from −30° C. to 250° C. from the standpoint of reactivity and yield. It is more preferably from 25° C. to 180° C. from the standpoint of reactivity and yield.

As described above, it has become possible to carry out convenient and economical industrial production of 2,6-dimethyl-1,5-heptadien-3-yl acetate (3), which is a sex pheromone component of Comstock mealybug, and 2,6-dimethyl-1,5-heptadien-3-ol (2), which is an intermediate thereof.

EXAMPLES

The present invention will hereinafter be described specifically with reference to Examples shown below. It should not be construed that the present invention is limited to or by Examples.

The term "purity" as used herein means an area percentage obtained by gas chromatography (GC) analysis unless otherwise particularly specified. The term "crude yield" means a yield determined without purification.

The GC conditions used are as follows:
GC: Capillary gas chromatograph GC-2010 produced by Shimadzu Corporation, column: DB-5 fixed-bed column having a size of 0.25 μm×0.25 mmϕ ×30 m, carrier gas: He (1.55 mL/min), detector: FID, column temperature: held at 60° C. for 3 minutes and then elevated to 250° C. at a rate of 10° C/min.

Synthesis Example 1

Production 1 of 2-methyl-3-buten-2-yl 2-methyl-2-propenyl ether (1)

After a reactor equipped with a stirrer, a condenser and a thermometer was purged with nitrogen, sodium hydride (55% dispersion in mineral oil, 52.4 g: 1.20 mol) and 1,2-dimethoxyethane (250.0 g) were added to the reactor, and the reaction mixture was heated to 35° C. Then the reaction mixture was subjected to dropwise addition of 2-methyl-3-buten-2-ol (107.7 g: 1.25 mol) at the reaction mixture temperature of from 40° C. to 50° C. over 3 hours, followed by stirring at the reaction mixture temperature of 50° C. for 2 hours. After the stirring, the resulting reaction mixture was subjected to dropwise addition of 2-methyl-2-propen-1-yl bromide (135.0 g: 1.0 mol) at the reaction mixture temperature of from 50° C. to 55° C. over one hour, followed by stirring at the reaction mixture temperature of 50° C. for 4 hours. The reaction of the resulting reaction mixture was terminated by addition of a 6.0% by weight aqueous ammonium chloride solution (380.0 g). The organic phase was separated from the water phase. The organic phase was washed with a 3.0 wt % aqueous sodium hydrogen carbonate solution (175.0 g) and then washed with an 8.0 wt % aqueous sodium chloride solution (185.0 g). The washed organic phase was subjected to solvent-removal under reduced pressure, and the residue was then purified by distillation to obtain 2-methyl-3-buten-2-yl 2-methyl-2-propenyl ether (1) (126.6 g: 0.90 mol, yield: 90.3%, purity: 98.6%).

Synthesis Example 2

Production 2 of 2-methyl-3-buten-2-yl 2-methyl-2-propenyl ether (1)

The 2-methyl-3-buten-2-yl 2-methyl-2-propenyl ether (1) was produced in the same manner as in Synthesis Example 1 except that 2-methyl-2-propen-1-yl chloride (90.6 g: 1.0 mol) was used in the place of the 2-methyl-2-propen-1-yl bromide and after dropwise addition of 2-methyl-2-propen-1-yl chloride, sodium iodide (7.4 g: 0.05 mol) was added to the reaction mixture. As a result, 2-methyl-3-buten-2-yl2-methyl-2-propenyl ether (1) (123.4 g: 0.88 mol, yield: 88.3%, purity: 98.1%) was produced.

Example 1

Production of 2,6-dimethyl-1,5-heptadien-3-ol (2)

After a reactor equipped with a stirrer, a condenser and a thermometer was purged with nitrogen, 2-methyl-3-buten-2-yl2-methyl-2-propenyl ether (1) (140.2 g: 1.0 mol) and tetrahydrofuran (700.0 g) were added to the reactor, and the reaction mixture was cooled to from −10° C. to −5° C. After cooling, the reaction mixture was subjected to dropwise addition of n-butyllithium (2.6 mol/L in a n-hexane solution, 461.5 mL: 1.20 mol) over 3 hours while keeping the temperature of the reaction mixture at from −5° C. to 0 ° C. After the dropwise addition, the reaction mixture was stirred at from −5° C. to 0° C. for 1 hour and then stirred at from 20° C. to 25° C. for 4 hours.

The reaction of the reaction mixture was terminated by addition of a 10.0 wt % aqueous ammonium chloride solution (630.0 g). The reaction mixture was extracted with n-hexane (280.0 g) to separate the organic phase from the water phase. The organic phase was washed with a 6.0% by weight aqueous sodium hydrogen carbonate solution (750.0 g), and then washed with a 10.0% by weight aqueous sodium chloride solution (430.0 g). The washed organic phase was subjected to removal of the solvent and low-boiling-point impurities under reduced pressure to obtain intended 2,6-dimethyl-1,5-heptadien-3-ol (2) (117.8 g: 0.84 mol, crude yield: 84.4%, purity: 81.0%).

Spectrum data of 2,6-dimethyl-1,5-heptadien-3-01 (2)

Nuclear magnetic resonance spectrum $^1$H-NMR (500 MHz, CDCl$_3$): δ1.02 (1H, d), 1.64 (3H, s), 1.72 (3H, d), 1.73 (3H, s), 2.26 (2H, dd), 4.04 (1H, t), 4.84 (1H, t), 4.95 (1H, t), 5.11 (1H, dt).
$^{13}$C-NMR (126 MHz, CDCl$_3$): δ17.95, 17.97, 25.87, 34.11, 75.19, 110.78, 119.71, 135.10, 147.04.
Mass spectrum EI (70 eV): m/z 140 (M$^+$), 122 (M$^+$-H$_2$O), 107, 107, 91, 79, 70, 55, 41, 27.
Infrared absorption spectrum (ATR analysis): ν (cm$^{-1}$) 835, 899, 1025, 1046, 1109, 1308, 1376, 1448, 1650, 2917, 2970, 3075, 3373.

Example 2

Production of 2,6-dimethyl-1,5-heptadien-3-ol (2)

The 2,6-dimethyl-1,5-heptadien-3-ol (2) was produced in the same manner as in Example 1 except that the dropwise addition of n-butyllithium was carried out while keeping the temperature of the reaction mixture at from −70° C. to −65° C. As a result, intended 2,6-dimethyl-1,5-heptadien-3-ol (2) (106.6 g: 0.76 mol, crude yield: 76.2%, purity: 78.0%) was obtained.

Example 3

Production of 2,6-dimethyl-1,5-heptadien-3-ol (2)

The 2,6-dimethyl-1,5-heptadien-3-ol (2) was produced in the same manner as in Example 1 except that the dropwise addition of n-butyllithium was carried out while keeping the temperature of the reaction mixture at from −35° C. to −30° C. As a result, intended 2,6-dimethyl-1,5-heptadien-3-ol (2) (119.2 g: 0.85 mol, crude yield: 84.5%, purity: 83.0%) was obtained.

Example 4

Production of 2,6-dimethyl-1,5-heptadien-3-ol (2)

The 2,6-dimethyl-1,5-heptadien-3-ol (2) was produced in the same manner as in Example 1 except that the amount of n-butyllithium was changed to 403.8 mL (1.05 mol). As a result, intended 2,6-dimethyl-1,5-heptadien-3-ol (2) (106.6 g: 0.76 mol, crude yield: 75.7%, purity: 76.7%) was obtained.

Example 5

Production of 2,6-dimethyl-1,5-heptadien-3-ol (2)

The 2,6-dimethyl-1,5-heptadien-3-ol (2) was produced in the same manner as in Example 1 except that the amount of n-butyllithium was changed to 538.4 mL (1.40 mol). As a result, intended 2,6-dimethyl-1,5-heptadien-3-ol (2) (122.0 g: 0.87 mol, crude yield: 86.7%, purity: 81.7%) was obtained.

Example 6

Production of 2,6-dimethyl-1,5-heptadien-3-ol (2)

The 2,6-dimethyl-1,5-heptadien-3-ol (2) was produced in the same manner as in Example 1 except that the amount of tetrahydrofuran was changed to 1400.0 g. As a result, intended 2,6-dimethyl-1,5-heptadien-3-ol (2) (122.0 g: 0.87 mol, crude yield: 86.7%, purity: 81.7%) was obtained.

Example 7

Production of 2,6-dimethyl-1,5-heptadien-3-ol (2)

The 2,6-dimethyl-1,5-heptadien-3-ol (2) was produced in the same manner as in Example 1 except that the amount of tetrahydrofuran was changed to 420 g. As a result, intended 2,6-dimethyl-1,5-heptadien-3-ol (2) (116.4 g: 0.83 mol, crude yield: 82.7%, purity: 81.2%) was obtained.

Example 8

Production of 2,6-dimethyl-1,5-heptadien-3-ol (2)

The 2,6-dimethyl-1,5-heptadien-3-ol (2) was produced in the same manner as in Example 1 except that lithium diisopropylamide (1.0 mol/L in a n-hexane and tetrahydrofuran solution, 1200.0 mL: 1.20 mol) was used in the place of n-butyllithium. As a result, intended 2,6-dimethyl-1,5-heptadien-3-ol (2) (115.0 g: 0.82 mol, crude yield: 81.8%, purity: 81.8%) was obtained.

Example 9

Production of 2,6-dimethyl-1,5-heptadien-3-yl acetate (3)

After a reactor equipped with a stirrer, a condenser and a thermometer was purged with nitrogen, 2,6-dimethyl-1,5- heptadien-3-ol (2) (140.2 g: 1.0 mol), acetonitrile (380.0 g) and pyridine (395.5 g: 5.0 mol) were added to the reactor. The reaction mixture was heated to 35° C., and subjected to dropwise addition of acetic anhydride (204.2 g: 2.0 mol) at the reaction mixture temperature of from 35° C. to 40° C. over 2 hours. After the dropwise addition, the temperature of the reaction mixture was elevated to 50° C. and stirred.

Water (380 g) was added to the reaction mixture to terminate the reaction. The reaction mixture was extracted with n-hexane (350.0 g) to separate the organic phase from the water phase. The organic phase was washed successively with 20% by weight aqueous hydrogen chloride (700.0 g), a 6.0% by weight aqueous sodium hydrogen carbonate solution (400.0 g), and a 10.0 wt % aqueous sodium chloride solution (300.0 g). The washed organic phase was subjected to solvent-removal under reduced pressure, and then the residue was purified by distillation to obtain 2,6-dimethyl-1,5-heptadien-3-yl acetate (3) (165.9 g: 0.91 mol, yield: 90.5%, purity: 97.9%).

Spectrum Data of 2,6-dimethyl-1,5-heptadien-3-yl acetate (3)

Nuclear magnetic resonance spectrum $^1$H-NMR (500 MHz, CDCl$_3$): δ1.60 (3H, s), 1.68 (3H, s), 1.72 (3H, s), 2.04 (3H, s), 2.32 (2H, ddt), 4.87 (1H, t), 4.93 (1H, s), 5.03 (1H, t), 5.14(1H, t).
$^{13}$C-NMR (126 MHz, CDCl$_3$): δ17.85, 18.31, 21.15, 25.70, 31.50, 77.00, 112.62, 118.93, 134.23, 143.01, 170.24.
Mass spectrum EI (70 eV): m/z 182 (M$^+$), 122 (M$^+$— CH$_3$CO$_2$H), 107, 91, 79, 69, 69, 53, 43.
Infrared absorption spectrum (ATR analysis): ν (cm$^{-1}$) 845, 903, 937, 1021, 1111, 1238, 1371, 1445, 1653, 1740, 2919, 2974.

Example 10

Production of 2,6-dimethyl-1,5-heptadien-3-yl acetate (3)

After a reactor equipped with a stirrer, a condenser and a thermometer was purged with nitrogen, 2,6-dimethyl-1,5-heptadien-3-ol (2) (140.2 g: 1.0 mol), toluene (150.0 g) and zinc chloride (2.2 g: 0.02 mol) were added to the reactor, and the reaction mixture was heated to 45° C. The resulting reaction mixture was subjected to dropwise addition of acetic anhydride (204.2 g: 2.0 mol) at the reaction mixture temperature of from 45° C. to 60° C. over 2 hours. After the dropwise addition, the reaction mixture was stirred at the reaction mixture temperature of 60° C.

Water (200 g) was added to the reaction mixture to terminate the reaction. The organic phase was separated from the water phase. The organic layer was washed successively with a 6.0% by weight aqueous sodium hydrogen carbonate solution (400.0 g) and a 10.0% by weight aqueous sodium chloride solution (300.0 g). The washed organic phase was subjected to solvent-removal under reduced pressure. The residue was purified by distillation to obtain 2,6-dimethyl-1,5-heptadien-3-yl acetate (3) (165.9 g: 0.91 mol, yield: 90.5%, purity: 95.8%).

What is claimed is:
1. A method for producing 2,6-dimethyl-1,5-heptadien-3-ol, comprising a step of subjecting 2-methyl-3-buten-2-yl 2-methyl-2-propenyl ether of formula (1):

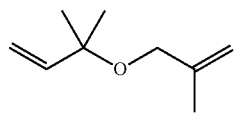

(1)

to a rearrangement reaction in the presence of a base to obtain 2,6-dimethyl-1,5-heptadien-3-ol of formula (2):

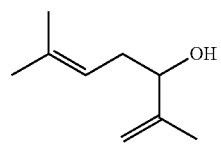

(2)

2. The method for producing 2,6-dimethyl-1,5-heptadien-3-ol according to claim 1, wherein the base is selected from the group consisting of metal alkoxides, organometallic compounds, and metal amides.

3. A method for producing 2,6-dimethyl-1,5-heptadien-3-yl acetate, comprising the steps of:
subjecting 2-methyl-3-buten-2-yl 2-methyl-2-propenyl ether of formula (1):

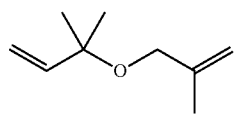

(1)

to a rearrangement reaction in the presence of a base to obtain 2,6-dimethyl-1,5-heptadien-3-ol of formula (2):

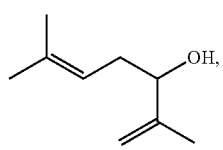

(2)

and
acetylating the 2,6-dimethyl-1,5-heptadien-3-ol to obtain 2,6-dimethyl-1,5-heptadien-3-yl acetate of formula (3):

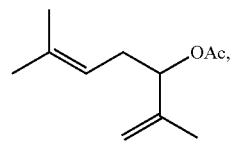

(3)

wherein Ac represents an acetyl group.
4. The method for producing 2,6-dimethyl-1,5-heptadien-3-yl acetate according to claim 3, wherein the base is selected from the group consisting of metal alkoxides, organometallic compounds, and metal amides.

* * * * *